(12) United States Patent
Pecherer et al.

(10) Patent No.: US 8,505,531 B2
(45) Date of Patent: Aug. 13, 2013

(54) HAND OPERATED ARTICULATED INTUBATION STYLET

(75) Inventors: Eugeny Pecherer, Netanya (IL); Shiri Soffer, Tel Aviv (IL)

(73) Assignee: Truphatek International Ltd., Netanya (IL)

( * ) Notice: Subject to any disclaimer, the term of this patent is extended or adjusted under 35 U.S.C. 154(b) by 805 days.

(21) Appl. No.: 12/451,507

(22) PCT Filed: May 15, 2007

(86) PCT No.: PCT/IL2007/000592
§ 371 (c)(1),
(2), (4) Date: Nov. 16, 2009

(87) PCT Pub. No.: WO2007/138569
PCT Pub. Date: Dec. 6, 2007

(65) Prior Publication Data
US 2010/0108060 A1    May 6, 2010

Related U.S. Application Data

(60) Provisional application No. 60/809,803, filed on Jun. 1, 2006.

(51) Int. Cl.
*A61M 16/00* (2006.01)
(52) U.S. Cl.
USPC ................................. 128/200.26; 128/207.14
(58) Field of Classification Search
USPC ......... 128/200.26, 207.14; 600/108; 604/35, 604/118, 119; 606/1
See application file for complete search history.

(56) References Cited

U.S. PATENT DOCUMENTS

| | | | |
|---|---|---|---|
| 2,865,374 A | 12/1958 | Brown et al. |
| 3,754,554 A | 8/1973 | Felbarg |
| 3,776,222 A | 12/1973 | Smiddy |
| 3,802,440 A | 4/1974 | Salem et al. |
| 3,854,473 A | 12/1974 | Matsuo |
| 3,996,939 A | 12/1976 | Sheridan et al. |
| 4,244,362 A | 1/1981 | Anderson |
| 4,245,624 A | 1/1981 | Komiya |
| 4,329,983 A | 5/1982 | Fletcher |
| 4,437,458 A | 3/1984 | Upsher |
| 4,498,473 A | 2/1985 | Gereg |
| 4,516,972 A | 5/1985 | Samson |
| 4,529,400 A | 7/1985 | Scholten |
| 4,756,708 A | 7/1988 | Martin |
| 4,793,327 A | 12/1988 | Frankel |

(Continued)

*Primary Examiner* — Elizabeth Houston
*Assistant Examiner* — Aundria Hairell
(74) *Attorney, Agent, or Firm* — Novick, Kim & Lee, PLLC; Harold L. Novick

(57) ABSTRACT

Hand operated articulated intubation stylet including an articulated stylet member with a link at its distal end, a L-shaped lever with a downward depending handle for tautening a flexible wire for flexing the link into a flexed positioned to form a hook-like configuration in the stylet member's side view, and a stopper mechanism mounted on the stylet member for stopping insertion of the stylet member into an endotracheal tube at a suitable position depending on the endotracheal tube's length. The handle and the link are on opposite sides of the stylet member such that a user conveniently operates the stylet with his fingers stretched out to grip the stylet member and his palm depressing the handle towards the stylet member to flex the stylet member's link into its flexed position for manipulating an endotracheal tube's outboard end for insertion into a patient's trachea.

18 Claims, 8 Drawing Sheets

(56) References Cited

U.S. PATENT DOCUMENTS

| | | | |
|---|---|---|---|
| 4,819,619 A | 4/1989 | Augustine et al. |
| 4,825,858 A | 5/1989 | Frankel |
| 4,827,925 A | 5/1989 | Vilasi |
| 4,898,577 A | 2/1990 | Badger et al. |
| 4,909,787 A | 3/1990 | Danforth |
| 4,949,716 A | 8/1990 | Chenoweth |
| 4,960,122 A | 10/1990 | Mizus |
| 4,976,688 A | 12/1990 | Rosenblum |
| 5,042,475 A | 8/1991 | LaBombard |
| 5,058,577 A | 10/1991 | Six |
| 5,095,888 A | 3/1992 | Hawley |
| 5,259,377 A | 11/1993 | Schroeder |
| 5,363,838 A | 11/1994 | George |
| 5,498,249 A | 3/1996 | Quinn |
| 5,643,221 A | 7/1997 | Bullard |
| 5,791,338 A | 8/1998 | Merchant et al. |
| 5,827,178 A | 10/1998 | Berall |
| 5,842,973 A | 12/1998 | Bullard |
| 5,846,183 A * | 12/1998 | Chilcoat ................ 600/136 |
| 5,951,461 A | 9/1999 | Nyo et al. |
| 5,973,728 A | 10/1999 | Levitan |
| 6,053,166 A | 4/2000 | Gomez |
| 6,123,666 A | 9/2000 | Wrenn et al. |
| 6,350,235 B1 | 2/2002 | Cohen et al. |
| 6,354,993 B1 | 3/2002 | Kaplan et al. |
| 6,432,042 B1 | 8/2002 | Bashour |
| 6,652,453 B2 | 11/2003 | Smith et al. |
| 6,655,377 B2 | 12/2003 | Pacey |
| 6,676,598 B2 | 1/2004 | Rudischauser |
| 6,761,171 B2 * | 7/2004 | Toti et al. ............ 128/207.14 |
| 6,840,903 B2 | 1/2005 | Mazzel |
| D642,262 S | 7/2011 | Wagner |
| D642,680 S | 8/2011 | Brucker et al. |
| D650,476 S | 12/2011 | Pecherer |
| 2005/0090712 A1 | 4/2005 | Cubb |
| 2007/0167686 A1 | 7/2007 | McGrath |

* cited by examiner

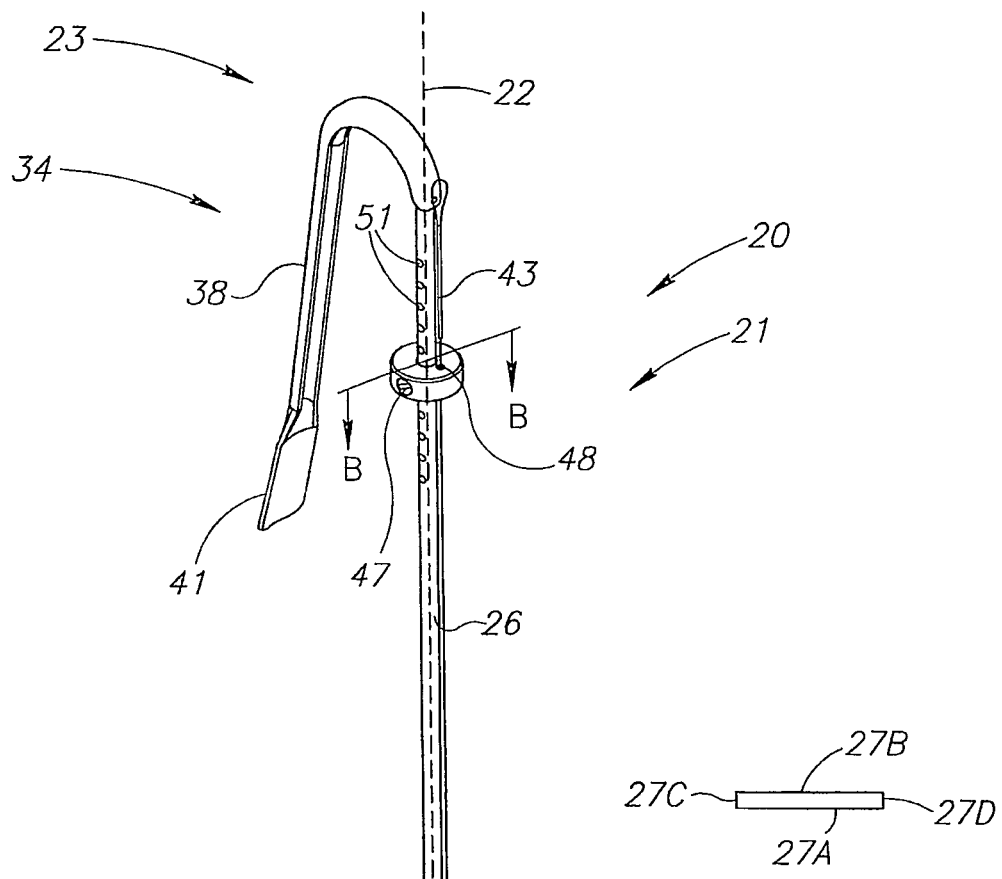
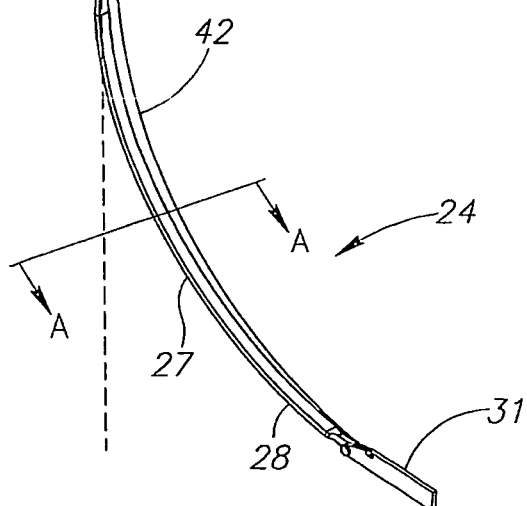
FIG.2B
FIG.2A

HAND OPERATED ARTICULATED INTUBATION STYLET

CROSS REFERENCE TO RELATED APPLICATIONS

This application is the U.S. National Application of PCT application Serial Number PCT/IL2007/000592 filed on 15 May 2007 in the English language and designating the United States, the entire contents of which are incorporated herein by reference; which PCT application claims priority on U.S. Provisional Patent Application Ser. No. 60/809,803 filed 1 Jun. 2006, the entire contents of which are incorporated herein by reference.

FIELD OF THE INVENTION

The invention pertains to hand operated articulated intubation stylets.

BACKGROUND OF THE INVENTION

Endotracheal tubes are utilized in a wide variety of medical procedures to provide an unobstructed air passage to a patient's trachea. In many emergency situations, it is necessary to intubate a patient as quickly as possible to provide a secure airway to the patient's lungs or permit forced ventilation thereof whilst preventing introduction of gastric contents. Intubation is often difficult because of the contours and obstacles encountered in a patient's airway. Perhaps the most difficult step in intubating a patient is maneuvering an endotracheal tube's outboard end into his trachea as opposed to his esophagus.

U.S. Pat. No. 4,329,983 to Fletcher illustrates and describes a guide device for an endotracheal tube which assists in intubating the trachea. The guide device includes a flexible bar which may be inserted in the endotracheal tube. A flexible line extends along the bar and has a free length at the inner end of the bar. When the line is pulled, the free length shortens and causes the inner end portion of the bar to flex in bowed fashion against the endotracheal tube.

U.S. Pat. No. 4,529,400 to Scholten illustrates and describes a directable stylet for naso and oroendotracheal intubations including hand operated lever bar and grip support for applying high force to an articulating wire that produces a first curvature and a reverse curvature to facilitate intubation.

Other stylets are illustrated and described in inter alia U.S. Pat. No. 3,854,47 to Matsuo, U.S. Pat. No. 3,996,939 to Sheridan et al., U.S. Pat. No. 4,244,362 to Anderson, U.S. Pat. No. 4,245,624 to Komiya, U.S. Pat. No. 4,898,577 to Badger et al, U.S. Pat. No. 4,909,787 to Danforth, U.S. Pat. No. 4,949,716 to Chenoweth, U.S. Pat. No. 4,960,122 to Mizus, U.S. Pat. No. 4,976,688 to Rosenblum, U.S. Pat. No. 5,042,475 to LaBombard, U.S. Pat. No. 5,058,577 to Six, U.S. Pat. No. 5,095,888 to Hawley, U.S. Pat. No. 5,259,377 to Schroeder, U.S. Pat. No. 5,498,249 to Quinn, and U.S. Pat. No. 5,791,338 to Merchant et al.

SUMMARY OF THE INVENTION

The present invention is directed towards hand operated articulated intubation stylets including an articulated stylet member with a link at its distal end, an L-shaped lever with a downward depending handle with a free end directed towards the stylet member's distal end for tautening a flexible wire for flexing the link into a flexed positioned to form a hook-like configuration in the stylet member's side view, and a stopper mechanism mounted on the stylet member for stopping the sliding insertion of the stylet member into an endotracheal tube at a suitable position depending on the endotracheal tube's length. The handle and the link are on opposite sides of the stylet member such that a user conveniently operates the stylet with his fingers stretched out to grip the stylet member and his palm depressing the handle towards the stylet member to flex the stylet member's link into its flexed position for manipulating an endotracheal tube's outboard end for insertion into a patient's trachea. The same stylet can be used with endotracheal tubes with a wide range of Inner Diameters (IDs) from about 5.5 mm to about 9 mm. The stylets can be made from metal or plastic components.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 2A is a perspective view of the stylet;

FIG. 2B is a cross section of the stylet member along line A-A in FIG. 2A;

DETAILED DESCRIPTION OF PREFERRED EMBODIMENT OF THE PRESENT INVENTION

Figure 1:
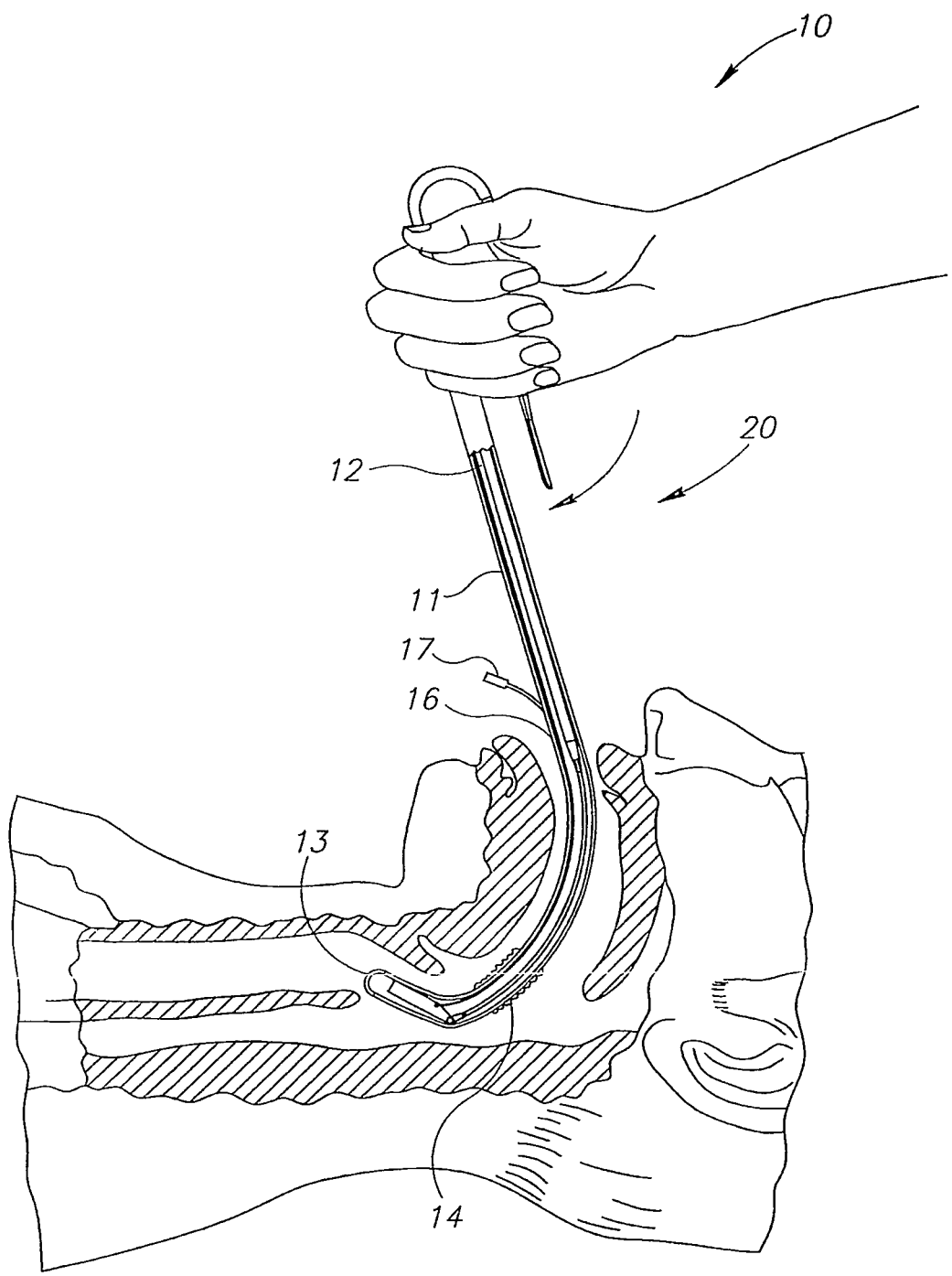
FIG. 1 is a diagrammatic view showing the use of an endotracheal intubation apparatus including a hand operated articulated intubation stylet with an articulated stylet member for manipulating an endotracheal tube's outboard end during an intubation procedure.
Figure 3:
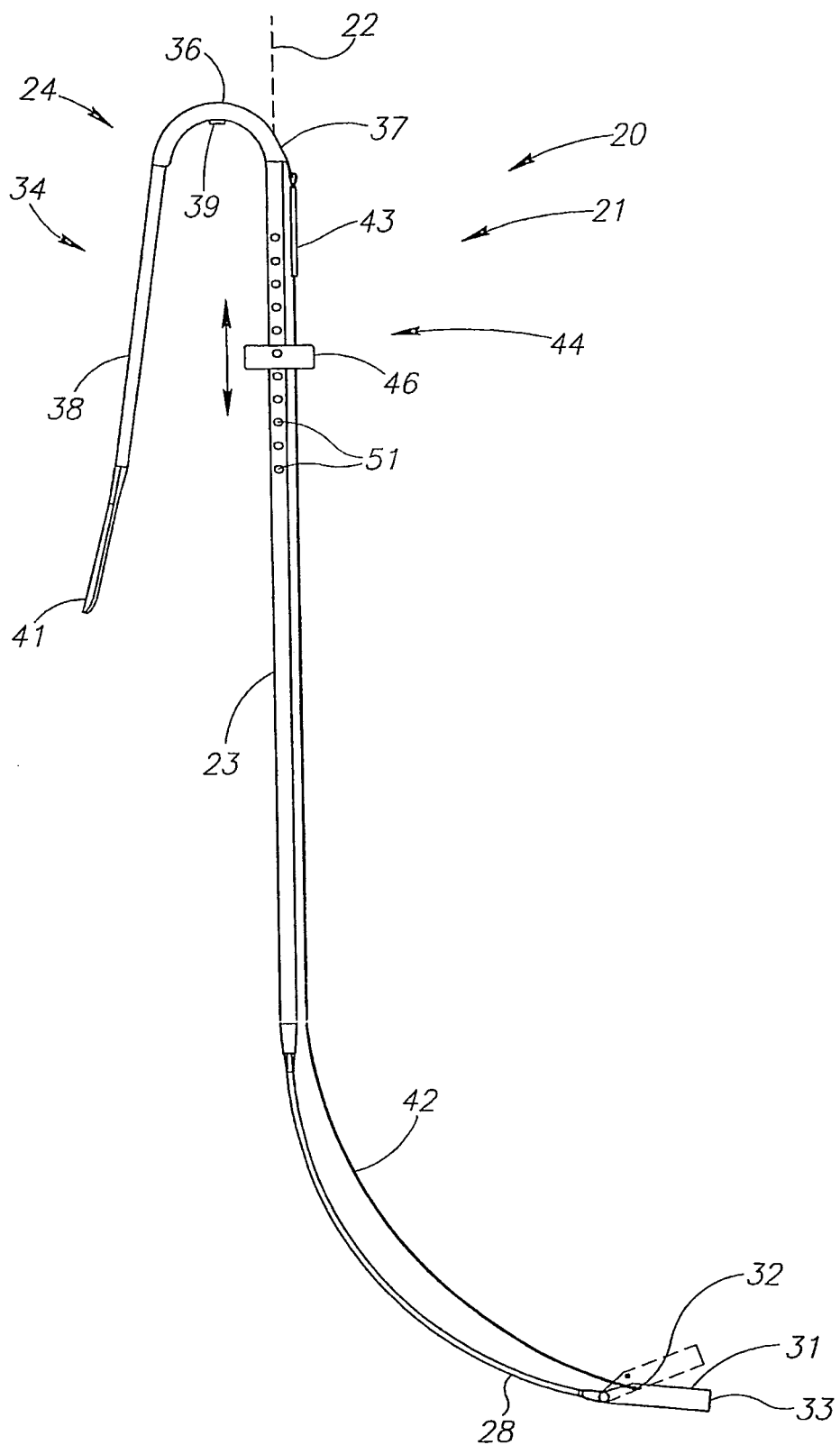
FIG. 3 is a side view of the stylet.
Figure 6:
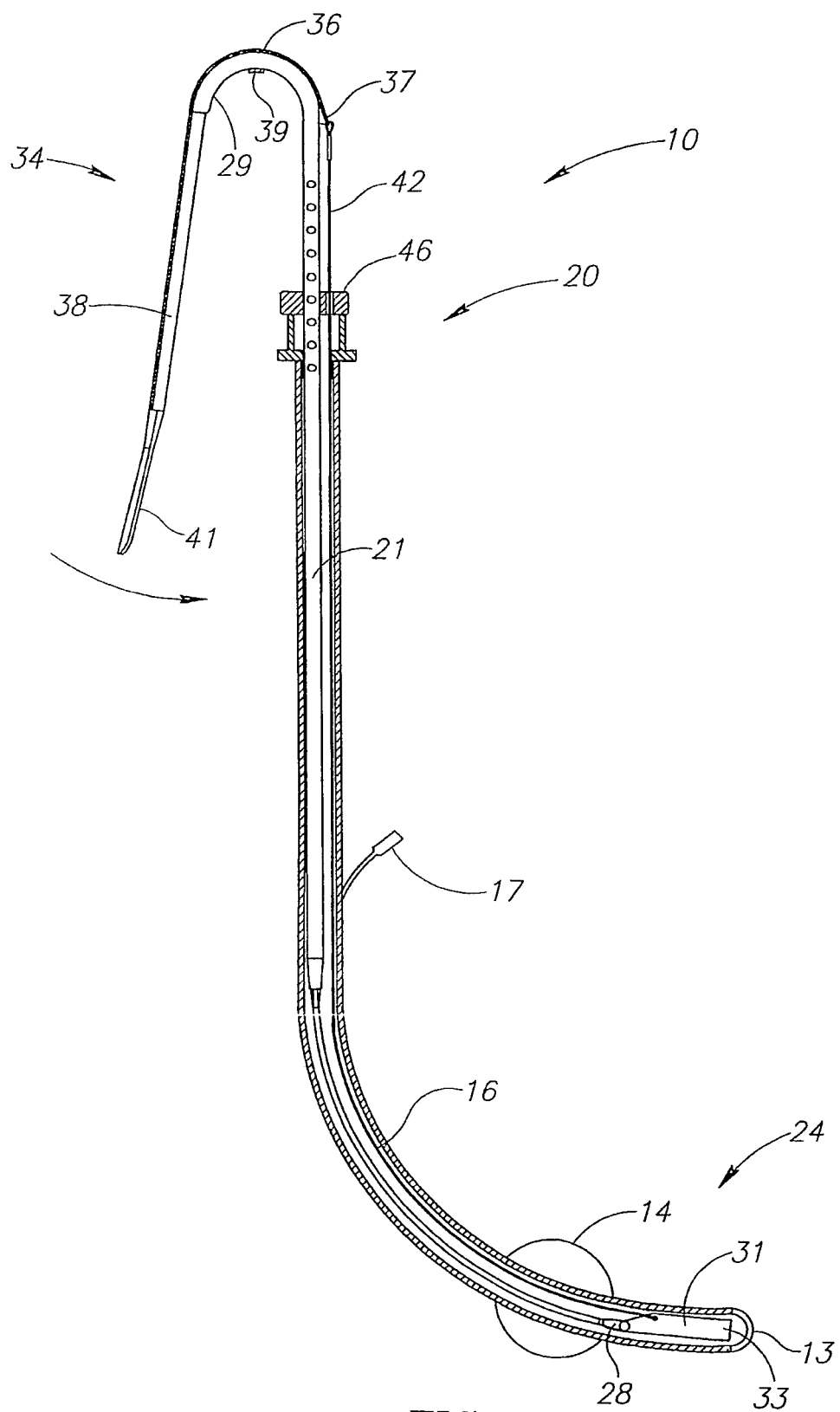
FIG. 6 is a partial longitudinal cross section of the endotracheal intubation apparatus in a set-up state.
Figure 7:
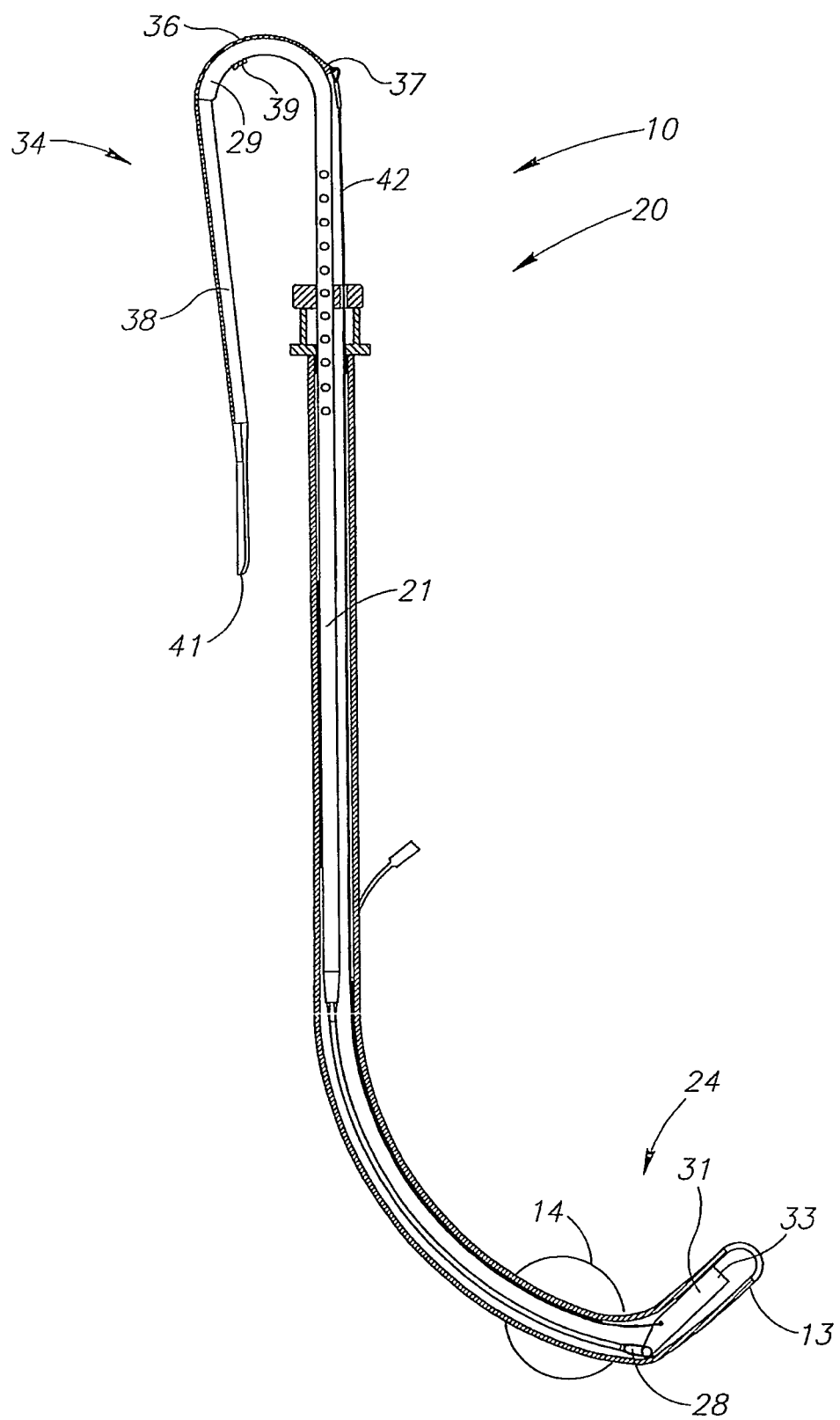
FIG. 7 is a partial longitudinal cross section of the endotracheal intubation apparatus in a flexed state.

FIGS. 1, 6 and 7 show an endotracheal intubation apparatus 10 including a flexible transparent hollow endotracheal tube 11 commercially available from Rusch International, Inc., USA, with an inboard end 12 and an outboard end 13. The outboard end 13 is provided with an endotracheal balloon 14 inflatable through an inflation line 16 fitted with a one way valve 17. FIG. 1 shows the balloon 14 deflated and FIGS. 6 and 7 show the balloon 14 inflated. The endotracheal intubation apparatus 10 also includes a hand operated articulated intubation stylet 20 for sliding insertion into the endotracheal tube 11 for assisting in manipulating the endotracheal tube's outboard end 13 into a patient's trachea as opposed to his esophagus.

FIGS. 2A, 3, 6 and 7 show the stylet 20 has an articulated stylet member 21 with a longitudinal axis 22 with a proximal end 23 and a distal end 24 diverging away from the longitudinal axis 22. The stylet member 21 includes an elongated rigid member 26 and a resiliently flexible leading segment 27 with a free end 28. The proximal end 23 has a curved free end 29 transversely directed to the longitudinal axis 22 on an opposite side to the stylet member 21 than the distal end 24 in FIG. 3. The segment 27 has a rectangular cross section with major front and rear surfaces 27A and 27B and a pair of minor side surfaces 27C and 28D (see FIG. 2B). The minor side surface 27C is visible in FIG. 3. The segment's free end 28 has an about 3 cm to an about 4 cm link 31 pivotally attached thereto. The link 31 is formed with an aperture 32 about a quarter away along towards its leading end 33. The link 31 is pivotable relative to the segment's free end 28 up to about 90° between an initial position generally co-directional with the distal end 24 and a flexed position with its leading end 33 directed towards the stylet member's proximal end 23 to form a hook-like configuration (shown in dashed contour in FIG. 3).

Figure 4:
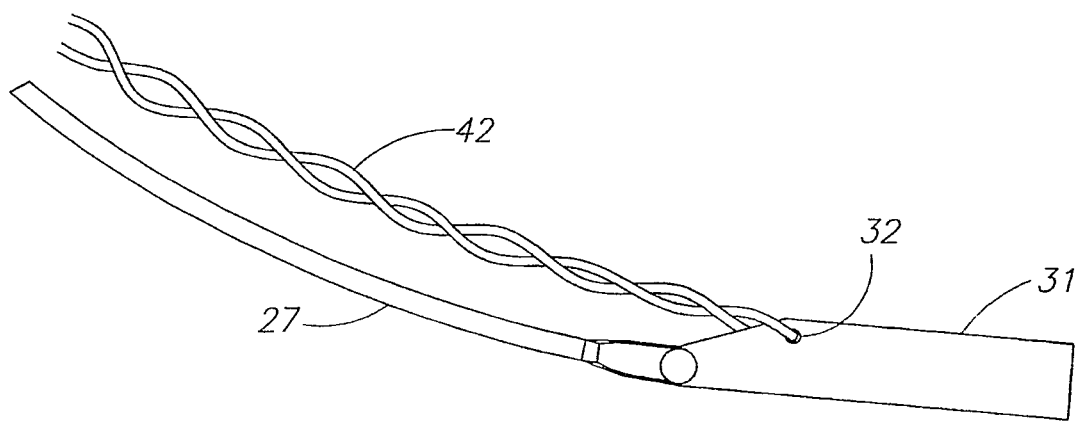
FIG. 4 is a close up view of the articulated stylet member's link.

The stylet 20 includes a generally L-shaped lever 34 displaceably mounted on the proximal end 23. The L-shaped lever 34 includes a short curved cross member 36 with a free end 37 and an elongated handle 38 on the opposite side to the stylet member 21 than the link 31 in FIG. 3. The curved cross member 36 is slidingly mounted on the curved free end 29 and retained thereon by a pair of opposite crimps 39. The handle 38 is co-directional with the stylet member 21 and directed toward the distal end 24, and has a free end 41. A flexible wire 42 extends between the curved cross member's free end 37 and the link's aperture 32. The wire 42 is constituted by a single length of braided wire passing through the link's aperture 32 (see FIG. 4). The wire's free ends are retained in a ferrule 43 attached to the curved cross member's free end 37. The wire 42 is preferably formed from 0.6 mm gauge stainless steel and is not elongated under the prevailing tensile forces. The wire 42 is dimensioned such that the handle's free end 41 is spaced apart from the stylet member 21 in its relaxed state. Depression of the handle's free end 41 towards the stylet member 21 tautens the wire 42 to urge the link 31 to assume the hook-like configuration.

Figure 5:
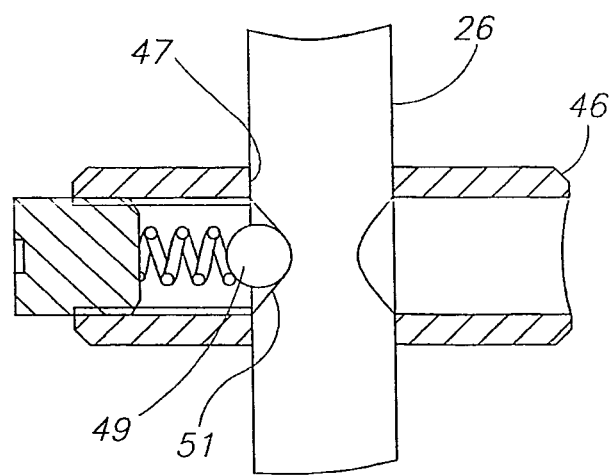
FIG. 5 is a transverse cross section of the stylet's stopper mechanism along line B-B in FIG. 2.

The stylet 20 includes a stopper mechanism 44 for stopping sliding insertion into the endotracheal tube 11 at a suitable position such that the same stylet 20 is suitable for use with endotracheal tubes 11 of different lengths. The stopper mechanism 44 includes a stopper 46 with a pair of spaced apart axial throughgoing bores 47 and 48 for passage of the stylet member 21 and the wire 42 therethrough. The stopper mechanism 44 includes a spring mounted ball bearing 49 for insertion into recesses 51 formed along the stylet member (see FIG. 5).

FIGS. 6 and 7 show the use of the endotracheal intubation apparatus 10 for manipulating an endotracheal tube's outboard end 13 for insertion into a patient's trachea during an intubation procedure. FIG. 6 shows the handle 38 in its set-up position with its free end 41 remote from the stylet member 21, the wire 42 in its relaxed state, and the link 31 in its set-up position generally co-directional with the stylet member's distal end 24. Initial depression of the handle 38 towards the stylet member 21 slides the curved cross member 36 on the curved free end 29 away from the stylet member 21 to tauten the wire 42 to begin to urge the link 31 to form its hook-like configuration with the segment's free end 28 urged against one of the endotracheal tube's inside surface and the link's free end 33 urged against the endotracheal tube's opposite inside surface. After taking up the slack, further depression of the handle's free end 41 towards the stylet member 21 further tautens the wire 42 to cause the link 31 to assume its full flexed position for raising the endotracheal tube's outboard end 13 for assisting in manipulating same into a patient's trachea.

Figure 8:
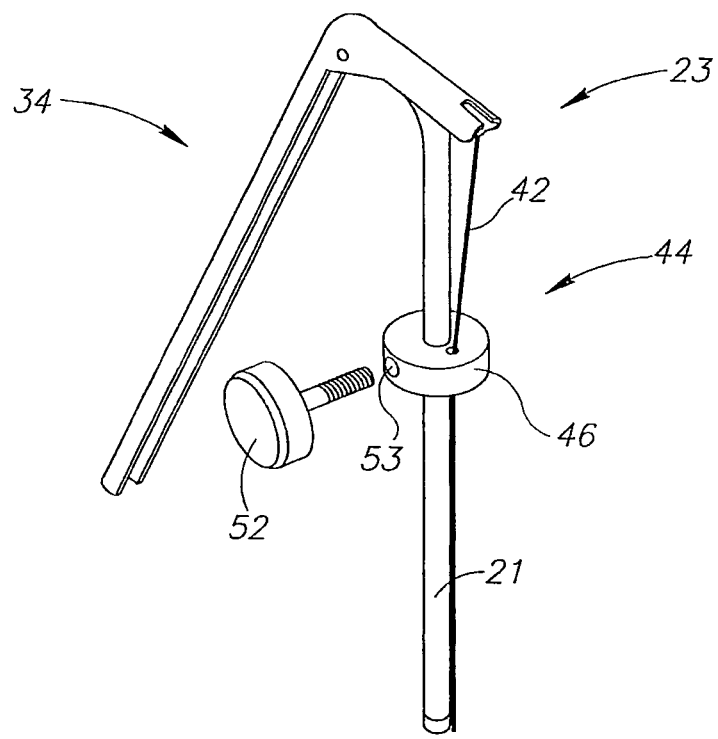
FIG. 8 is an isometric view of an alternative L-shaped lever and a screw based stopper mechanism.

FIG. 8 shows an alternative L-shaped lever 34 pivotably mounted on the stylet member's proximal end 23 as opposed to be slidingly mounted thereon, and an alternative stopper mechanism 44 including a screw 52 for screw thread insertion into a radial throughgoing bore 53 for stopping the stopper 46 at different positions along the stylet member 21.

Figure 9:
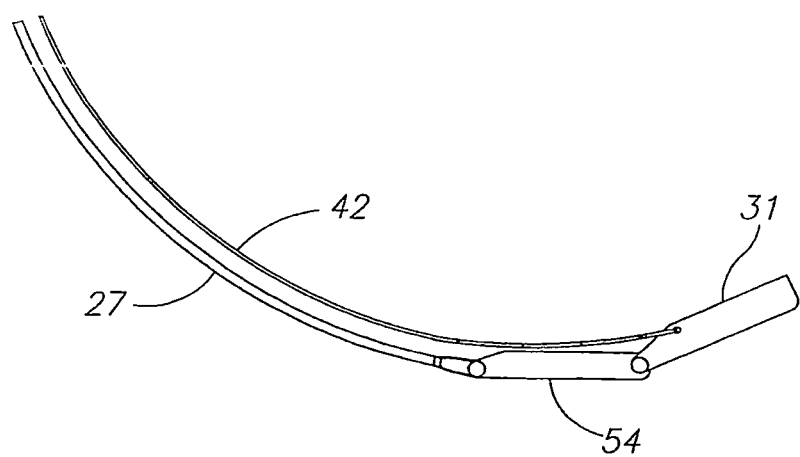
FIG. 9 is a side view of an alternative embodiment of the articulated stylet member's distal end with multiple links.

FIG. 9 shows the stylet member 21 can include one or more additional links 54 to replace at least some of the resiliently flexible leading segment.

Figure 10:
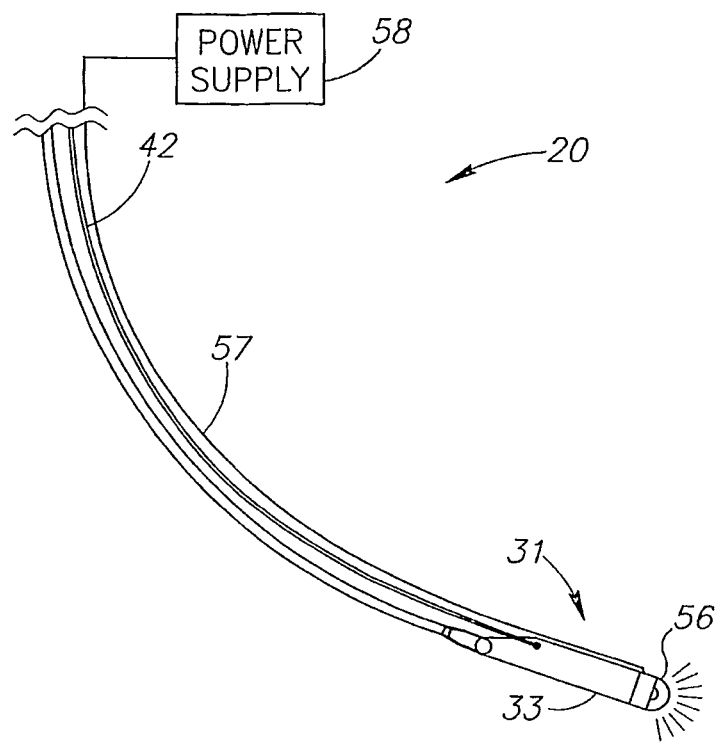
FIG. 10 is a side view of an alternative embodiment of the articulated stylet member's distal end with a light source.

FIG. 10 shows the stylet 20 can include a light source 56 at the link's leading end 33 and a single insulated electrical wire 57 connecting a power supply 58 to the light source 57 for energizing same for illumination purposes. The stylet 20 closes the electrical circuit illuminating the light source 56.

Figure 11:
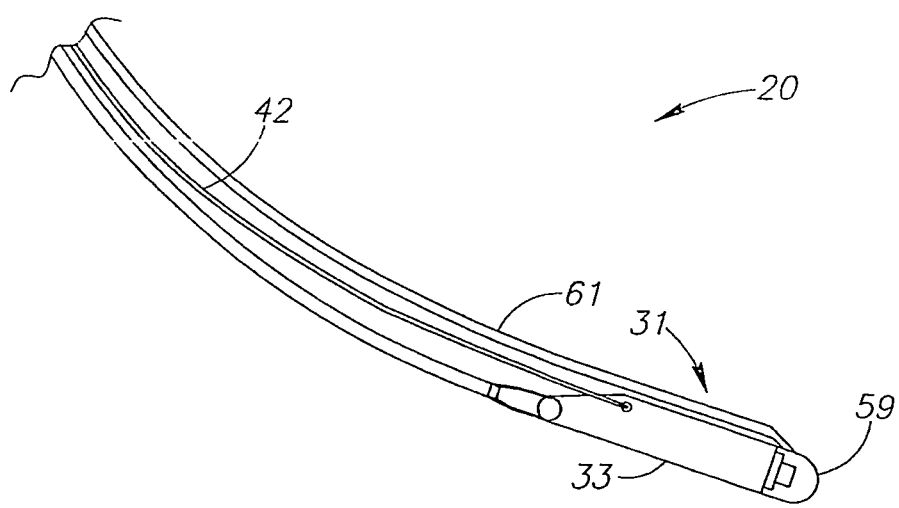
FIG. 11 is a side view of an alternative embodiment of the articulated stylet member's distal end with an imaging device.

FIG. 11 shows the stylet 20 can include an imaging device 59 at the link's leading end 33 and a wire bundle 61 for imaging purposes.

While the invention has been described with respect to a limited number of embodiments, it will be appreciated that many variations, modifications, and other applications of the invention can be made within the scope of the appended claims.

The invention claimed is:

1. Hand operated articulated intubation stylet for use with an endotracheal tube including a flexible hollow tube member with an inboard end and an outboard end, the stylet comprising:
 (a) an articulated stylet member for sliding insertion into the endotracheal tube from its inboard end towards its outboard end, said stylet member having a longitudinal axis and. including an elongated rigid member with a proximal end and with a distal end that diverges away from said longitudinal axis in a side view of said stylet member,
 said proximal end having a curved free end and transversely directed to said longitudinal axis on an opposite side to said stylet member than said distal end, and
 a link pivotably attached to said distal end and having a leading end remote from said distal end, said link being pivotable between an initial position generally co-directional with said distal end and a flexed position with said link's leading end directed toward said stylet member's proximal end to form a hook-like configuration in said side view for manipulating the endotracheal tube's outboard end for insertion into a patient's trachea;
 (b) a hand operated generally L-shaped lever having a short curved cross member and an elongated handle with a free handle end, said short curved cross member having a free cross member end disposed towards said longitudinal axis,
 said L-shaped lever being mounted on said stylet member's proximal end with said short curved cross member transversely directed with respect to said stylet member and said elongated handle on an opposite side to said stylet member than said link in said side view and co-directional with said stylet member with said free handle end directed toward said distal end,
 said short curved cross member of said L-shaped lever being slidingly disposed on said curved free end of said proximal end in a transverse direction to said longitudinal axis;
 (c) a flexible wire extending between said cross member and said link; and (d) a stopper mechanism mounted on said stylet member for stopping sliding insertion of said stylet member into the endotracheal tube at a suitable position depending on the endotracheal tube's length, whereby the arrangement being such that said L-shaped lever handle is manually depressible from a set-up state with said free handle end distanced from said longitudinal axis to a flexing state with its free handle end adjacent said longitudinal axis and said curved cross member having transversely slid on said curved free end relative to said longitudinal axis for tautening said wire for urging said link from said initial position to said flexed position.

2. The stylet as claimed in claim 1 wherein said stylet member includes a resiliently flexible leading segment toward said distal end, said resiliently flexible leading segment having a rectangular cross section with major front and rear surfaces, and minor side surfaces, one of said minor side surfaces being visible in said side view.

3. The stylet as claimed in claim 1 wherein said stylet member includes at least one additional link between said distal end and said link.

4. The stylet as claimed in claim 1 wherein said stopper mechanism includes a stopper with a pair of spaced apart axial throughgoing bores for passage of said stylet member and said wire therethrough, and a spring biased ball bearing for stopping said stopper along said stylet member at a desired position therealong for determining the desired insertion of said stylet member into the endotracheal tube.

5. The stylet as claimed in claim 1 wherein said stopper mechanism includes a stopper with a pair of spaced apart axial throughgoing bores for passage of said stylet member and said wire therethrough, and a screw for stopping said stopper along said stylet member at a desired position therealong for determining the desired insertion of said stylet member into the endotracheal tube.

6. The stylet as claimed in claim 1 wherein said wire is constituted by a single length of wire folded in half and passing through an aperture formed in said link.

7. The stylet as claimed in claim 6 wherein said wire is braided.

8. The stylet as claimed in claim 1 and further comprising a light source at said stylet member's distal end.

9. The stylet as claimed in claim 1 and further comprising an imaging device at said stylet member's distal end.

10. A hand operated articulated intubation stylet for use with an endotracheal tube including a flexible hollow tube member with an inboard end and an outboard end, the stylet comprising
(a) an articulated stylet member for sliding insertion into the endotracheal tube from its inboard end towards it outboard end, said stylet member having a longitudinal axis and including an elongated rigid member with a curved proximal end and with a distal end that diverge away from said longitudinal axis in a side view of said stylet member,
and a link pivotably attached to said distal end and having a leading end remote from said distal end, said link being pivotable between an initial position generally co-directional with said distal end and a flexed position with said link's leading end directed toward said stylet member's proximal end to form a hook-like configuration in said side view for manipulating the endotracheal tube's outboard end for insertion into a patient's trachea;
(b) a hand operated generally L-shaped lever having a short curved cross member and an elongated handle with a free handle end, said short curved cross member having a free cross member end disposed towards said longitudinal axis,
said L-shaped lever being slidingly mounted on said stylet member's proximal end with said curved cross member transversely directed with respect to said longitudinal axis, said curved cross member of said L-shaped lever being slidingly disposed on said curved proximal end of said stylet member in a transverse direction to said longitudinal axis;
(c) a flexible wire extending between said cross member and said link, and
(d) a stopper mechanism mounted on said stylet member for stopping sliding insertion of said stylet member into the endotracheal tube at a suitable position depending on the endotracheal tube's length,
whereby the arrangement being such that said L-shaped lever is manually depressible from a set-up state with said free handle end distanced from said longitudinal axis to a flexing state with its free handle end adjacent said longitudinal axis and said curved cross member having transversely slid on said curved free end relative to said longitudinal axis for tautening said wire for urging said link from said initial position to said flexed position.

11. The stylet as claimed in claim 10 wherein said stylet member includes a resiliently flexible leading segment toward said distal end, said resiliently flexible leading segment having a rectangular cross section with major front and rear surfaces, and minor side surfaces, one of said minor side surfaces being visible in said side view.

12. The stylet as claimed in claim 10 wherein said stylet member includes at least one additional link between said distal end and said link.

13. The stylet as claimed in claim 10 wherein said stopper mechanism includes a stopper with a pair of spaced apart axial throughgoing bores for passage of said stylet member and said wire therethrough, and a spring biased ball bearing for stopping said stopper along said stylet member at a desired position therealong for determining the desired insertion of said stylet member into the endotracheal tube.

14. The stylet as claimed in claim 10 wherein said stopper mechanism includes a stopper with a pair of spaced apart axial throughgoing bores for passage of said stylet member and said wire therethrough, and a screw for stopping said stopper along said stylet member at a desired position therealong for determining the desired insertion of said stylet member into the endotracheal tube.

15. The stylet as claimed in claim 10 wherein said wire is constituted by a single length of wire folded in half and passing through an aperture formed in said link.

16. The stylet as claimed in claim 15 wherein said wire is braided.

17. The stylet as claimed in claim 10 and further comprising a light source at said stylet member's distal end.

18. The stylet as claimed in claim 10 and further comprising an imaging device at said stylet member's distal end.

* * * * *